(12) United States Patent
Mukaidani et al.

(10) Patent No.: US 7,871,980 B2
(45) Date of Patent: Jan. 18, 2011

(54) METHOD OF TREATING MOUSE CARRYING HUMAN HEPATOCYTES

(75) Inventors: Chise Mukaidani, Higashihiroshima (JP); Katsutoshi Yoshizato, Higashihiroshima (JP); Norio Masumoto, Higashihiroshima (JP); Miho Kataoka, Kumamoto (JP); Tatsuhiko Tsunoda, Yokohama (JP); Fuyuki Miya, Yokohama (JP)

(73) Assignees: Hiroshima Industrial Promotion Organization, Hiroshima (JP); Biointegrence Inc., Hiroshima (JP); Riken, Saitama (JP)

( * ) Notice: Subject to any disclaimer, the term of this patent is extended or adjusted under 35 U.S.C. 154(b) by 130 days.

(21) Appl. No.: 11/988,028

(22) PCT Filed: Jun. 30, 2006

(86) PCT No.: PCT/JP2006/313077
§ 371 (c)(1),
(2), (4) Date: Mar. 18, 2008

(87) PCT Pub. No.: WO2007/004547
PCT Pub. Date: Jan. 11, 2007

(65) Prior Publication Data
US 2009/0060882 A1 Mar. 5, 2009

(30) Foreign Application Priority Data
Jun. 30, 2005 (JP) .............................. 2005-193015

(51) Int. Cl.
*C12N 5/08* (2006.01)
*A01N 63/00* (2006.01)
*A61K 38/27* (2006.01)

(52) U.S. Cl. ...................... 514/11.4; 435/370; 424/93.7
(58) Field of Classification Search ...................... None
See application file for complete search history.

(56) References Cited

U.S. PATENT DOCUMENTS

| 6,017,884 | A | 1/2000 | Ichida et al. |
| 7,560,279 | B2 * | 7/2009 | Mukaidani et al. .......... 435/370 |
| 2002/0187936 | A1 * | 12/2002 | Costa et al. ................... 514/12 |
| 2005/0255591 | A1 | 11/2005 | Mukaidani et al. |

FOREIGN PATENT DOCUMENTS

| JP | 9-136840 | 5/1997 |
| JP | 2005-504010 | 2/2005 |
| WO | 03/080821 | 10/2003 |

OTHER PUBLICATIONS

Tateno et al., American Journal of Pathology, 165(3):901-912, Sep. 2004.*
Masumoto et al., Journal of Endocrinology, 194:529-537, 2007.*

* cited by examiner

*Primary Examiner*—Marianne P Allen
(74) *Attorney, Agent, or Firm*—Wenderoth, Lind & Ponack, L.L.P.

(57) ABSTRACT

Human adult hepatocytes are transplanted into an immunodeficient hepatopathy mouse and then human growth hormone is administered to the mouse to thereby elevate twice or more the replacement ratio by the human adult hepatocytes having been transplanted. Further, human growth hormone is administered to an immunodeficient hepatopathy mouse carrying human young hepatocytes transplanted thereinto so as to improve fatty liver of the mouse in which about 70% or more of the hepatocytes have been replaced by the human hepatocytes.

2 Claims, 7 Drawing Sheets

*P < 0.05

Fig. 3
Steatosis grade
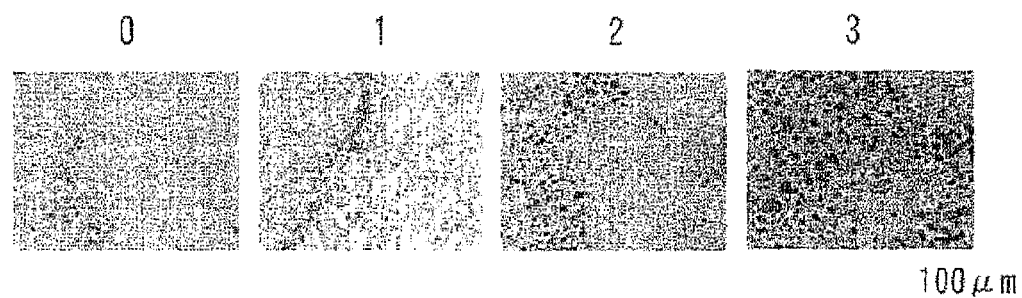
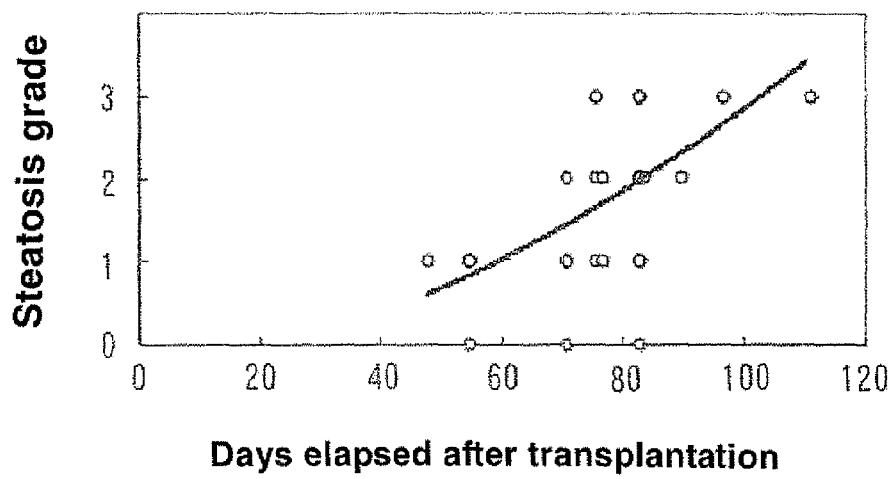
Days elapsed after transplantation

METHOD OF TREATING MOUSE CARRYING HUMAN HEPATOCYTES

TECHNICAL FIELD

The present invention relates to a method of treating a mouse carrying human hepatocytes (hereinafter sometimes referred to as a "human hepatocyte chimeric mouse"). More particularly, the present invention relates to a treatment method characterized by administering human growth hormone to a human hepatocyte chimeric mouse.

BACKGROUND ART

In drug development, the stage of selection of drug candidate substances is of the highest interest to the pharmaceutical companies. It is common knowledge that enormous research and development cost of 30 billion yen or more and a period of 10 years or longer is required for the drug development. Therefore, it must be avoided that the drug candidate substance halts the development in the middle of the research and development. In preclinical studies, animals such as monkeys, dogs, rats and mice are used, however, it is known that a drug metabolic activity is greatly different between animals and humans. Because of the species difference of drug metabolic activity between humans and animals, development is halted in the stage of clinical studies with respect to about half the drug candidate substances.

In human hepatocyte chimeric mice, human pharmacokinetics can be reproduced in a state close to the case where evaluation is performed in human individuals. Therefore, it is considered that they can be used for the prediction of human pharmacokinetics in drug development. From these, human hepatocyte chimeric mice are considered to be effective as a tool for predicting metabolism or toxicity in humans in drug development. Further, if it becomes possible to produce chimeric mice carrying hepatocytes of a patient himself, it becomes possible to realize personalized medicine that can be used for considering dosing strategy or treatment method suitable for the pathologic conditions of the patient.

The present inventors succeeded in producing a human hepatocyte chimeric mouse in which 70% or more of the mouse liver was replaced with human hepatocytes by producing a uPA/SCID mouse which is obtained by mating a mouse (uPA-Tg mouse) into which urokinase plasminogen activator (uPA) gene ligated to an enhancer and a promoter of albumin was introduced with a SCID mouse, transplanting human hepatocytes into this mouse and administering a complement inhibitor (Patent document 1).

However, even in the method of Patent document 1, high replacement with human hepatocytes (70% or more) can be achieved in the case where young human hepatocytes (the age confirmed in Patent document 1 is 14 years or younger) are transplanted, and even if hepatocytes of an adult human who is 40 years old or older are transplanted into a uPA/SCID mouse, the replacement ratio is 5% or less in most of the cases.

There are some cases where the degree of drug metabolic activity is different between young human hepatocytes and adult human hepatocytes depending on, for example, the type of drug, therefore, the necessity of human hepatocyte chimeric mice in which the replacement with adult human hepatocytes is achieved at a high ratio is extremely high for drug metabolism or toxicity screening. Further, also in the case where chimeric mice carrying hepatocytes of a patient himself are produced for personalized medicine, adult human hepatocyte chimeric mice with high replacement are necessary for therapy for adult diseases.

Incidentally, it has been revealed that growth hormone promotes the proliferation of hepatocytes mediated by the expression of Foxm1B gene in hepatocytes, and it is known that by administering growth hormone to aged mice whose liver was excised, the growth potential of hepatocytes can be restored to the same level as that of young mice after the liver was excised (Non-patent document 1). In this connection, a method of treating a liver disease and liver damage using growth hormone and FoxM1B (Patent document 2), and a therapeutic agent for acute hepatic failure containing human growth hormone as an active ingredient (Patent document 3) are known, respectively. Further, IGF-1 (insulin-like growth factor-1) is also known as a hepatocyte growth factor, and it is also known that its expression is increased by growth hormone (for example, Non-patent documents 2 and 3).

On the other hand, as described above, in the liver of chimeric mice transplanted with young human hepatocytes, the replacement ratio with human hepatocytes reaches 70% or more on about day 60 after transplantation. These human hepatocytes on about day 60 after transplantation are morphologically similar to hepatocytes in the normal human liver, however, lipid droplets are gradually accumulated in hepatocytes thereafter in some cases. The chimeric mouse showing such fatty liver symptoms is useful as a fatty liver animal model, however, it is not suitable as a tool for studying the drug efficacy or toxicity for human liver. Accordingly, a means for improving fatty liver symptoms occurring in human hepatocyte chimeric mice with high replacement has been demanded.

Patent document 1: WO 03/080821 A1

Patent document 2: JP-T-2005-504010

Patent document 3: JP-A-9-136840

Non-patent document 1: K., Krupczak-Hollis, et al, Hepatology, 2003, 38:

Non-patent document 2: Velasco B., et al., Eur. J. Endocrinol. 2001, 145(1): 73-85

Non-patent document 3: Bartke A. et al., Proc. Soc. Exp. Biol. Med. 1999, 222(2): 113-23

DISCLOSURE OF INVENTION

As described above, mice with high replacement with human hepatocytes by the method of Patent document 1 are obtained only in the case where young human hepatocytes are transplanted, and the replacement ratio in the case where adult human liver is transplanted is about 5% or less in many cases.

The necessity of chimeric mice in which the replacement with adult human hepatocytes has been achieved at a high ratio is extremely high as a screening system for drug metabolism or toxicity in adult humans, or a screening system for the most suitable therapeutic method for personalized medicine.

A first object of the present invention is to provide a method capable of increasing a replacement ratio with adult human hepatocytes in a chimeric mouse by about twice or more.

Further, in the case where young human hepatocytes are transplanted, about 70% or more of mouse hepatocytes can be replaced with human hepatocytes. However, in this case, the human hepatocytes sometimes show fatty liver symptoms, therefore, it had a problem as a system for studying drug efficacy test or toxicity test for normal human hepatocytes or the like.

A second object of the present invention is to provide a method of improving fatty liver in a human hepatocyte chimeric mouse with high replacement.

This application provides as a first invention for achieving the above objects, a method of increasing a replacement ratio with adult human hepatocytes in an immunodeficient hepatopathy mouse by twice or more, comprising the steps of:

(1) transplanting adult human hepatocytes into the immunodeficient hepatopathy mouse; and (2) administering human growth hormone to the mouse transplanted with adult human hepatocytes.

That is, the inventors of this application succeeded in increasing a ratio (replacement ratio) of adult human hepatocytes to mouse hepatocytes by about twice or more by administering human growth hormone to the chimeric mouse transplanted with the adult human hepatocytes thereby to specifically proliferate the transplanted hepatocytes. Such an effect depends on the species specificity of the growth hormone. As described above, growth hormone promotes the proliferation of hepatocytes (adult human hepatocytes) with reduced growth potential, however, human growth hormone particularly strongly acts on human hepatocytes due to its species specificity. Therefore, administration of human growth hormone to an adult human hepatocyte chimeric mouse has a low proliferative effect on the hepatocytes of host mouse (that is, it does not restore the liver damage of mouse), and proliferates only the transplanted adult human hepatocytes. As a result, the replacement ratio with human hepatocytes derived from adult human hepatocytes is increased by about twice or more compared with the case where a treatment with growth hormone was not performed.

Further, this application provides, as a second invention, a method of improving fatty liver in an immunodeficient hepatopathy mouse transplanted with young human hepatocytes, comprising the step of administering human growth hormone to the mouse transplanted with young human hepatocytes.

That is, the inventors of this application succeeded in improving fatty liver occurring in the human hepatocyte chimeric mouse with high replacement by administering human growth hormone for a given period of time.

Incidentally, growth hormone is useful for maintaining a normal function of hepatocytes (such as expression of IGF-1). Therefore, administration of human growth hormone to a human hepatocyte chimeric mouse does not block the function of human hepatocytes of the chimeric mouse, but rather restores the human hepatocytes to a more normal state (a state close to that of hepatocytes in the human liver).

In the present invention, the term "adult human hepatocytes" means, for example, hepatocytes isolated from a human who is 20 years old or older, particularly 40 years old or older, which show a low replacement ratio when they are transplanted into a mouse by the method of Patent document 1. Further, the term "young human hepatocytes" means hepatocytes isolated from a human who is 0 years old or older and under 20 years old, particularly 0 years old or older and 14 years old or younger, which show a high replacement ratio when they are transplanted into a mouse by the method of Patent document 1 and as a result, they show fatty liver symptoms.

In the first invention, the phrase "increasing a replacement ratio by twice or more" means that, for example, a replacement ratio of about 5%, which is a general replacement ratio when adult human hepatocytes are transplanted into a mouse, is increased to a replacement ratio of about 10% or more. Alternatively, it means that, for example, in the case where a replacement ratio with human hepatocytes when hepatocytes isolated from an adult human patient are transplanted into a mouse is 10%, the replacement ratio when the hepatocytes are transplanted is increased to about 20% or more by administering human growth hormone.

In the second invention, the phrase "improving fatty liver" means that the structure and/or function of hepatocytes are/is made equal or similar to those/that of normal hepatocytes by reducing or removing accumulation of lipid droplets in hepatocytes. Further, it also includes the prevention of occurrence of fatty liver symptoms beforehand.

Other modes, terms and concepts according to the respective inventions described above will be defined in detail in the description of embodiments of the invention and Examples. In addition, various techniques to be used for carrying out this invention can be easily and surely performed by those skilled in the art on the basis of known literatures and the like except for the techniques whose references are particularly specified. For example, the techniques of genetic engineering and molecular biology of this invention are described in Sambrook and Maniatis, in Molecular Cloning—A Laboratory Manual, Cold Spring Harbor Laboratory Press, New York, 1989; Ausubel, F. M. et al., Current Protocols in Molecular Biology, John Wiley & Sons, New York, N.Y. 1995, and the like. Further, materials and methods to be used in the respective inventions refer to the contents of disclosure of Patent document 1 (WO 03/080821 A1).

BRIEF DESCRIPTION OF DRAWINGS

FIG. 3 shows the results showing the number of days elapsed after transplantation and the degree of steatosis in chimeric mice transplanted with hepatocytes of a female child.

BEST MODE FOR CARRYING OUT THE INVENTION

Figure 1:
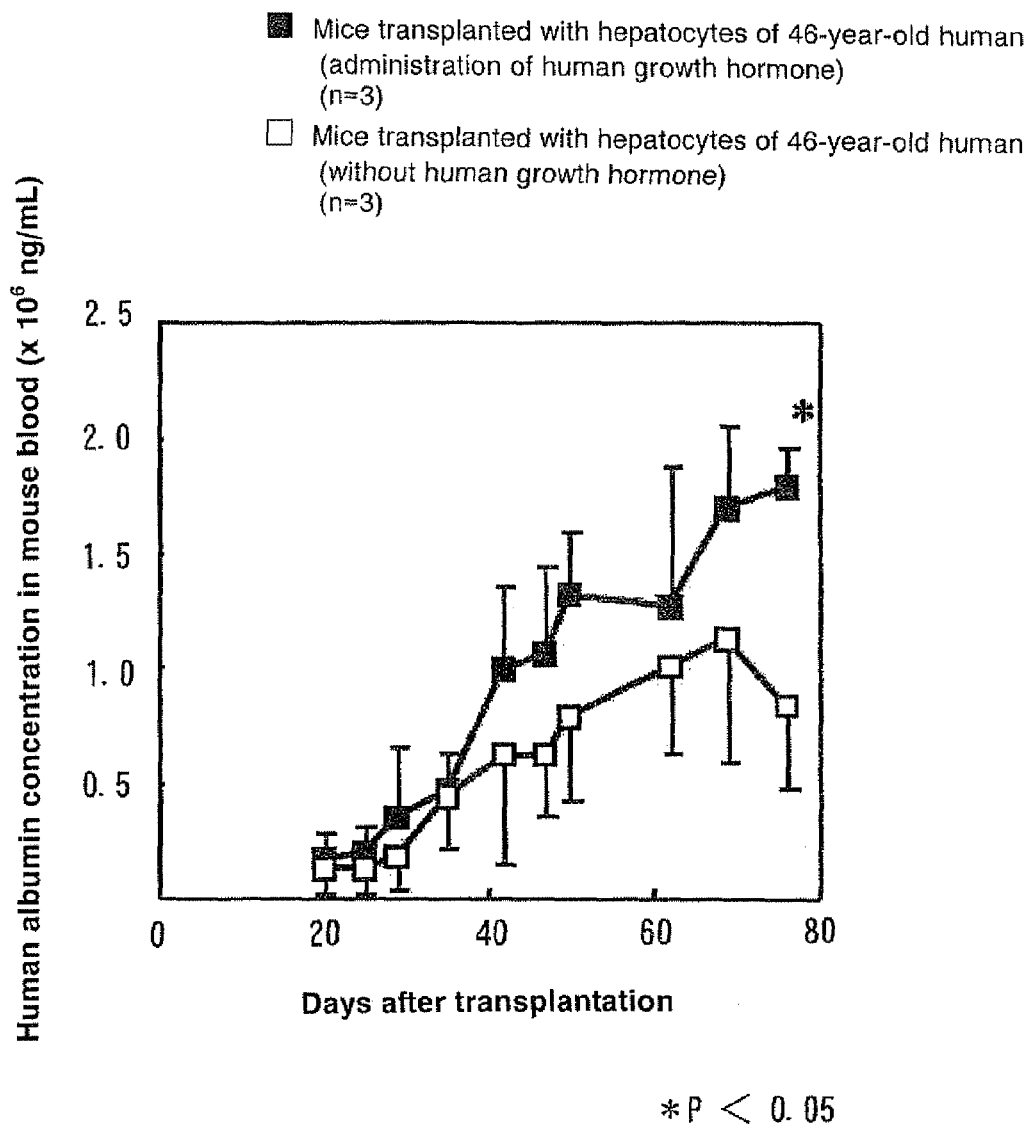
FIG. 1 shows the results showing the average value of human albumin concentration in mouse blood measured over time in a group in which human growth hormone was administered to nice transplanted with hepatocytes of an adult human male and a group in which the human growth hormone was not administered to the mice.

In the step (1) according to the first invention, an adult human hepatocyte chimeric mouse is produced by transplanting adult human hepatocytes into an immunodeficient hepatopathy mouse. The immunodeficient hepatopathy mouse to be used in this step is a "hepatopathy mouse" in which the original hepatocytes of the mouse are damaged and a "immunodeficient mouse" which does not show rejection of cells derived from a xenogeneic animal as described in Patent document 1. Such an immunodeficient hepatopathy mouse can be produced by subjecting the same individual mouse to a treatment for inducing hepatopathy (for example, a treatment with a known hepatopathy-inducing substance) and a treatment for inducing immunodeficiency (for example, administration of an immunosuppressive agent or thymectomy). Further, it is also preferred to use a mouse with genetic immunodeficiency and hepatopathy produced by mating a mouse with genetic hepatopathy (for example, uPA-Tg mouse) with a mouse with genetic immunodeficiency (SCID mouse, NUDE mouse, RAG2 knockout mouse, or the like). Further, as disclosed in Patent document 1, it is preferred to use a mouse in which the hepatopathy gene is homozygous as the mouse with genetic immunodeficiency and hepatopathy. However, even a hemizygous mouse with genetic immunodeficiency and hepatopathy can be used as the mouse of this invention by performing a pretreatment with a substance that specifically inhibits the normal hepatocyte growth (for example, a kind of pyrrolizidine alkaloid such as retrorsine, lasiocarpine, seneciphylline, monocrotaline or trichodesmine).

As adult human hepatocytes to be transplanted, hepatocytes isolated by a known colagenase perfusion method or the like from liver tissues excised by a known technique from an adult human liver are used. Alternatively, hepatocytes which are isolated in this way and are cryopreserved can also be used after being thawed.

Such adult human hepatocytes can be transplanted into the liver of a mouse through the spleen. Further, they can also be transplanted directly from the portal vein. The number of human hepatocytes to be transplanted can be set to 1 to around 1000000.

Subsequently, in the step (2), human growth hormone is administered to the adult human hepatocyte chimeric mouse. As the human growth hormone, commercially available recombinant human growth hormone can be used. The administration can be started before transplantation of human hepatocytes, or from an arbitrary point of time after the transplantation. As for the administration, subcutaneous administration is performed according to an appropriate schedule (for example, once per 1 to 3 days) or continuous administration is performed by implantation of an osmotic pump under the skin. The dose can be set to about 0.1 to 10.0 μg per 1 g of body weight of mouse.

The second invention is a method of improving fatty liver in a human hepatocyte chimeric mouse with high replacement, which comprises the step of administering human growth hormone to the mouse transplanted with young human hepatocytes (that is, a mouse in which the replacement with human hepatocytes may be achieved at a high ratio or a mouse in which the replacement with human hepatocytes has been achieved at a high ratio).

The human hepatocyte chimeric mouse with high replacement can be produced by, for example, the method described in Patent document 1. That is, it is a "hepatopathy mouse" in which the original hepatocytes of the mouse are damaged and a "immunodeficiency mouse" which does not show rejection of cells derived from a xenogeneic animal as described in Patent document 1. Such an immunodeficient hepatopathy mouse can be produced by subjecting the same individual mouse to a treatment for inducing hepatopathy (for example, a treatment with a known hepatopathy-inducing substance) and a treatment for inducing immunodeficiency (for example, administration of an immunosuppressive agent or thymectomy). Further, it is also preferred to use a mouse with genetic immunodeficiency and hepatopathy produced by mating a mouse with genetic hepatopathy (for example, uPA-Tg mouse) with a mouse with genetic immunodeficiency (SCID mouse, NUDE mouse, RAG2 knockout mouse, or the like). Further, as disclosed in Patent document 1, it is preferred to use a mouse in which the hepatopathy gene is homozygous as the mouse with genetic immunodeficiency and hepatopathy. However, even a hemizygous mouse with genetic immunodeficiency and hepatopathy can be used as the mouse of this invention by performing a pretreatment with a substance that specifically inhibits the normal hepatocyte growth (for example, a kind of pyrrolizidine alkaloid such as retrorsine, lasiocarpine, seneciphylline, monocrotaline or trichodesmine).

As hepatocytes to be transplanted, hepatocytes isolated by a known collagenase perfusion method or the like from liver tissues excised by a known technique from a young human liver are used. Alternatively, hepatocytes which are isolated in this way and are cryopreserved can also be used after being thawed. Commercially available hepatocytes can also be used.

Such young human hepatocytes can be transplanted into the liver of a mouse through the spleen. Further, they can also be transplanted directly from the portal vein. The number of human hepatocytes to be transplanted can be set to 1 to around 1000000.

In the thus produced human hepatocyte chimeric mouse, on about 60 days after transplantation, 70% or more of the hepatocytes are replaced with human hepatocytes. This 70% or more replacement can be confirmed by, for example, an increase in the human albumin concentration (about 6 mg/mL or more) in mouse blood. The human hepatocytes of such a chimeric mouse has a tendency to show fatty liver symptoms thereafter. Accordingly, to the chimeric mouse transplanted with young human hepatocytes, human growth hormone is administered. The administration can be started before transplantation of human hepatocytes, or from an arbitrary point of time after the transplantation. Further, according to the intended use of the chimeric mouse, the administration can also be started after 70% or more replacement is achieved. In this case, for example, human growth hormone is continuously administered for 1 to 4 weeks starting from 60 to 70 days after transplantation of human hepatocytes. With regard to the administration method, for example, subcutaneous administration is performed on consecutive days, or continuous administration is performed by implantation of an osmotic pump under the skin. As the human growth hormone, commercially available recombinant human growth hormone can be used. The dose can be set to about 0.1 to 10.0 μg per 1 g of body weight of mouse.

Hereinafter, the invention of this application will be described in further detail and specifically with reference to Examples, however, the invention of this application is not limited to the following examples.

EXAMPLES

Example 1

Administration of Human Growth Hormone to uPA/SCID Mice Transplanted with Adult Human Hepatocytes 1-1. Test Substance In order to evaluate the growth potential of human hepatocyte chimeric mice, recombinant human growth hormone (Wako Pure Chemical Industries, Ltd.) was used.

1-2. Animals

As recipient animals, uPA/SCID mice which are mice having a property of immunodeficiency and hepatopathy were produced in Hiroshima Prefectural Institute of Industrial Science and Technology according to Patent document 1 and used. Cryopreserved hepatocytes of a 46-year-old male human (manufactured by In Vitro Technology Inc.) were thawed according to the literature (Tateno C. et al., Am. J. Pathol. 2004 165: 901-912.4) and used.

1-3. Transplantation and Administration

Into eight uPA(+/+)/SCID mice, $7.5 \times 10^5$ cells of human hepatocytes were transplanted through the spleen. On day 26 after transplantation, the mice were divided into a group with administration of human growth hormone and a group without administration. The human growth hormone was dissolved in 100 µL of endotoxin-free water, and subcutaneously administered once daily every day at a dose of 2.5 µg/g of body weight.

1-4. Determination of Human Albumin Concentration in Mouse Blood

The human albumin concentration in the blood was determined once a week using the latex bead immunoturbidimetry (Eiken Chemical Co., Ltd.).

1-5. Determination of Replacement Ratio with Human Hepatocytes

The liver was excised on day 76 after transplantation from each of the uPA(+/+)/SCID mice transplanted with human hepatocytes. Frozen sections were prepared from the excised liver, and immunostaining was performed using a human-specific cytokeratin 8/18 antibody (ICN Pharmaceuticals, Inc.) which specifically reacts with human hepatocytes. The ratio of cytokeratin 8/18 antibody-positive area to the total section area was determined to be a replacement ratio with human hepatocytes.

2. Results

Figure 2:
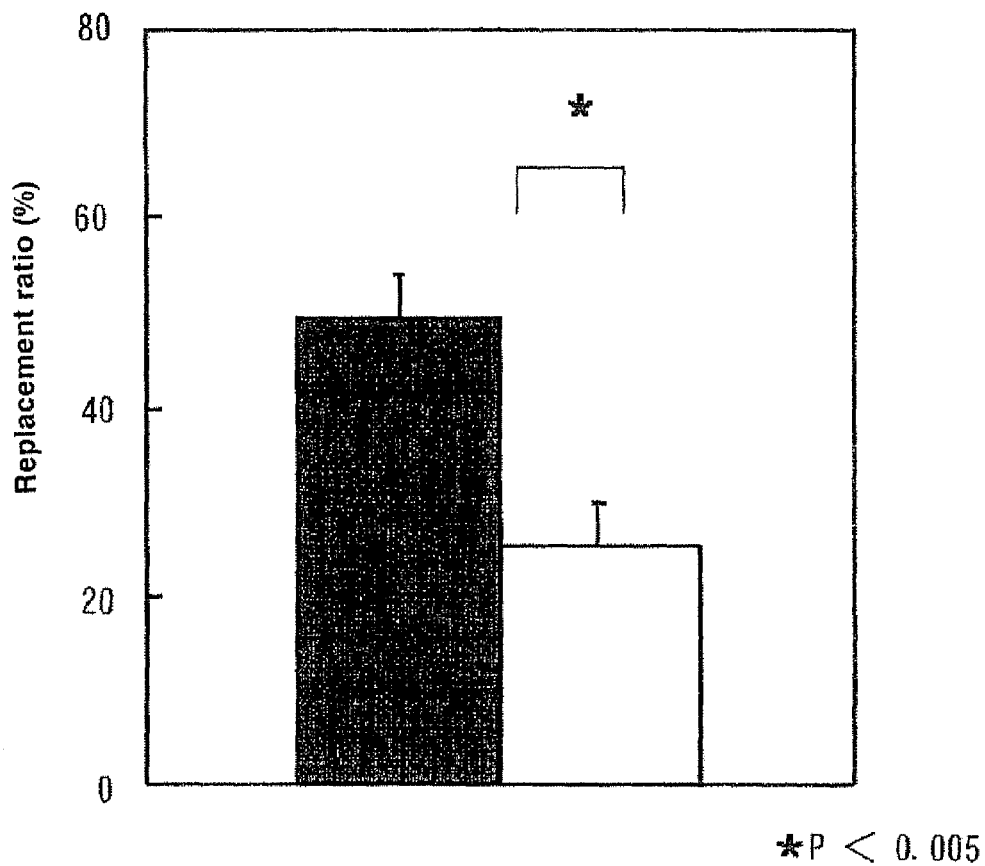
FIG. 2 shows the results showing the average value and standard deviation of replacement ratio of liver on day 76 after transplantation in mice in a group in which human growth hormone was administered to mice transplanted with hepatocytes of an adult human male and a group in which the human growth hormone was not administered to the mice.

Cryopreserved hepatocytes of an adult male human (46 years old) were thawed and $1.0 \times 10^6$ cells of the hepatocytes were transplanted into each of uPA(+/+)/SCID mice Six chimeric mice which have almost the same human albumin concentration in mouse blood were selected. Then, from day 26 after transplantation, administration of human growth hormone at a dose of 2.5 mg per 1 g of body weight was started for three mice, and for the remaining three mice, administration was not performed. As a result, on day 76 after transplantation, the human albumin concentration was higher in the group with administration of human growth hormone by about 1.8-fold than in the group without administration (FIG. 1). The liver of each of the mice was excised on day 76 after transplantation, and immunostaining was performed using a human-specific cytokeratin 8/18 antibody. As a result, the replacement ratio in the group with administration of human growth hormone was higher by about 2.0-fold than in the group without administration (FIG. 2). From the above results, it was confirmed that by administration of human growth hormone, the growth potential of transplanted adult human hepatocytes became higher and chimeric mice with higher replacement ratio could be obtained.

Example 2

Short-Term Administration of Human Growth Hormone to uPA/SCID Mice Transplanted with Young Human Hepatocytes 1-1. Test Substance In order to evaluate the growth potential of human hepatocyte chimeric mice, recombinant human growth hormone (Wako Pure Chemical Industries, Ltd.) was used.

1-2. Animals

As recipient animals, uPA(+/+)/SCID mice which are mice having a property of liver damage and immunodeficiency were produced in Hiroshima Prefectural Institute of Industrial Science and Technology according to Patent document 1 and used. As donor hepatocytes, cryopreserved hepatocytes of a 6-year-old female child (manufactured by BD Gentest Inc.) or a 9-month-old male child (manufactured by In Vitro Technology Inc.) were thawed according to the literature (Tateno C. et al., Am. J. Pathol. 2004 165: 901-912.4) and used.

1-3 Transplantation and Administration

Into forty-one uPA(+/+)/SCID mice, $7.5 \times 10^5$ cells of the donor hepatocytes of a 6-year-old female child were transplanted, and into six uPA(+/+)/SCID mice, $7.5 \times 10^5$ cells of the donor hepatocytes of a 9-month-old male child were transplanted through the spleen, and chimeric mice were produced according to Patent document 1. The chimeric mice transplanted with hepatocytes of a 6-year-old female child were killed between 48 days and 111 days after transplantation, and the blood and liver were collected. In 6 mice among the 41 mice, an osmotic pump filled with human growth hormone was implanted under the skin for 14 days before they were killed. The human growth hormone was dissolved in endotoxin-free water, and the solution was packed in the osmotic pump such that the dose became 2.5 µg/g of body weight per day. The skin on the back was incised, the osmotic pump was inserted under the skin, and the skin was sutured. Frozen sections of the liver were prepared, and Oil Red O lipid staining was performed Stained specimens were photographed. The degree of steatosis was graded into 4 grades from to 4 according to the degree of the Oil Red O-positive lipid droplets, and the liver of each mouse was evaluated. The case in which lipid deposition was hardly observed in hepatocytes was graded 0, the case in which lipid deposition was observed in 33% or less of hepatocytes was graded 1 (slight), the case in which lipid deposition was observed in 33 to 66% or more of hepatocytes was graded 2 (moderate), and the case in which lipid deposition was observed in 66% or more of hepatocytes was graded 3 (high) (Matteoni, C. A. et al.: Nonalcoholic fatty liver disease: a spectrum of clinical and pathological severity. Gastroenterology, 116: 1413-1419, 1999). In 3 mice among the 6 chimeric mice transplanted with hepatocytes of a 9-month-old male child, an osmotic pump was implanted in the same manner as above at 2 weeks before they were killed such that the dose became 2.5 µg/g of body weight per day. Then, the 6 mice were killed between days 72 and 101 after transplantation, and hepatocytes were collected.

1-4. Determination of Human Albumin and Human IGF-1 Concentrations in Mouse Blood 2 µL of the blood was collected from the tail and the human albumin concentration was determined once a week using the latex bead immunoturbidimetry (Eiken Chemical Co., Ltd.). The human IGF-1 concentration in the serum of each of 3 mice without administration of growth hormone and 3 mice with administration thereof among the chimeric mice transplanted with hepatocytes of a 6-year-old female child was determined using an ELISA method (R&D Systems).

1-5. Isolation of Chimeric Mouse Hepatocytes

From each of three 9-month-old male child chimeric mice without administration of growth hormone and three 9-month-old male child chimeric mice with administration of growth hormone, a cell dispersion was obtained by a collagenase perfusion method. The cell dispersion was subjected to low-speed centrifugation at 50 g for 2 minutes, whereby the precipitate and supernatant were separated. A portion of hepatic parenchymal cells of the precipitate was dissolved in RLT buffer and stored at −80° C. in a deep freezer. With a portion of the cells antibody K8216, which is specific to human hepatocytes and was produced by the present inventors (hybridoma K8216 strain (deposited with International Patent Organism Depositary, National Institute of Advanced Industrial Science and Technology in Japan as FERM P-18751, and also deposited with International Depository Center as FERM BP-8333), was allowed to react at 4° C. for 30 minutes, washing with PBS was performed three times, and then, FITC-labeled rat IgG antibody was allowed to react with the cells for 30 minutes. After washing with PBS was performed three times, the cells were dispersed in Dulbecco's Modified Eagle's Medium containing 10% fetal bovine serum. Then, an analysis was performed by FACS Vantage (Vecton Dickinson), and the ratio of human hepatocytes in the hepatocytes was obtained.

1-6. Isolation of Human Hepatocytes from Excised Liver

In Hiroshima University Hospital, informed consent was obtained from 4 cases of patients (25 to 61 years old) who had surgical excision of a portion of liver, and normal liver tissues were isolated from a surface different from the cut surface of the excised liver. The liver tissues were immediately perfused with UW solution after excision, and transported to a clean room dedicated to human cells while keeping them in UW solution at 4° C. Perfusion was performed from a thick vessel in the cut surface of the liver tissues with a buffer containing EGTA for about 20 minutes using an injection syringe. Then, perfusion was performed with a buffer containing collagenase until the tissues became soft. Thereafter, liver capsule was stripped and cells were dispersed in a medium. The cell dispersion was subjected to low-speed centrifugation at 50 g, whereby the precipitate and supernatant were separated. A portion of hepatic parenchymal cells of the precipitate was dissolved in RLT buffer and stored at −80° C. in a deep freezer.

1-7. Determination of mRNA Expression Level in Chimeric Mouse Hepatocytes

Total RNA was extracted from hepatocytes collected from the chimeric mice and excised liver using RNeasy Mini Kit (QIAGEN), and the RNA samples were treated with RNase-Free DNase Set (QIAGEN). From 1 mg of the total RNA, cDNA was synthesized using PowerScript reverse transcriptase and Oligo dt (12-18) primer. By using the resulting cDNA as a template, and using a primer set specific to human genes and SYBR Green PCR master mix (Applied Biosystems), the expression level of mRNA was determined by quantitative real-time RT-PCR with PRISM 7700 sequence detector (Applied Biosystems). The ratio thereof to the expression level of a reference sample was obtained according to the delta-delta CT method from the number of cycles of human IGF-1, human IGFALS (Insulin-like growth factor-1 binding protein, acid labile subunit), human SOCS2 (suppressor of cytokine signaling 2), human FADS1 (fatty acid desaturase 1), human FADS2 (fatty acid desaturase 2), human FASN (fatty acid synthetase), human SCD (stearoyl-CoA desaturase) and human GAPDH (glyceraldehydes 3-phosphate dehydrogenase). Correction was performed by dividing the respective expression levels by the expression level of GAPDH.

2. Results

Evaluation was performed in terms of fatty lesion of the liver of 6-year-old female child chimeric mice killed between 48 days and 111 days after transplantation Until 60 days after transplantation, the steatosis grade was between 0 and 1, which was low, and lipid droplets were few. From 70 days after transplantation, the steatosis grade increased, and large lipid droplets were observed, and sometimes found in the entire region of hepatocytes (FIG. 3). This indicated that in the liver of chimeric mice, fatty change was not observed much until around 60 days after transplantation, however, the number of mice in which fatty change was observed increased from 70 days after transplantation, and the degree of fatty change increased with the days elapsed after transplantation.

Figure 4:
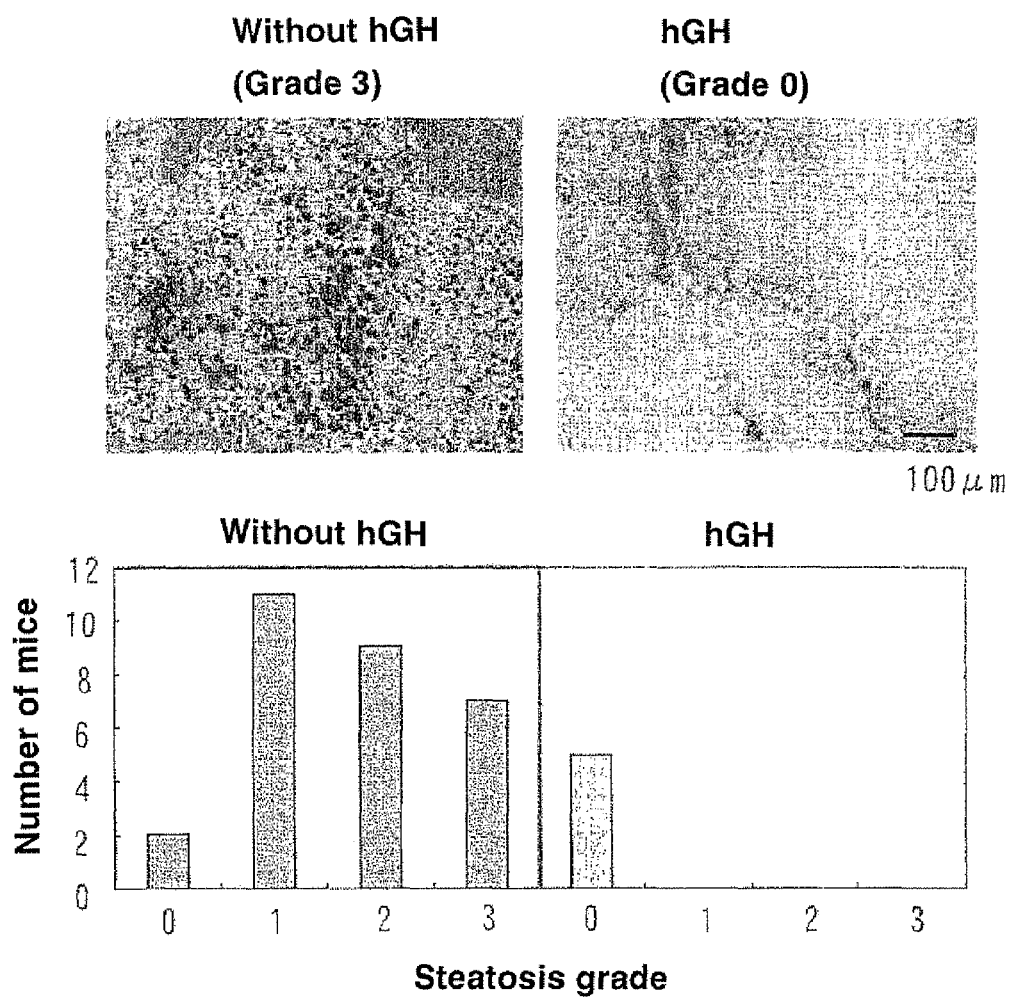
FIG. 4 shows the results showing the image stained with oil red O and the degree of steatosis of the liver of chimeric mice transplanted with hepatocytes of a female child between 70 and 90 days after transplantation with and without administration of human growth hormone.

Evaluation of fatty lesion of the liver of 6-year-old female child chimeric mice between 70 and 90 days after transplantation was performed for mice with administration of human growth hormone (5 mice) and mice without administration (29 mice). As a result, in the mice without administration, the percentage of the mice with grade 1 or higher was 93%, however, in the mice with administration, all the 5 mice showed grade 0 (FIG. 4). This indicated that by continuously administering human growth hormone to chimeric mice on 70 days after transplantation or thereafter for 2 weeks, steatosis was ameliorated.

Figure 5:
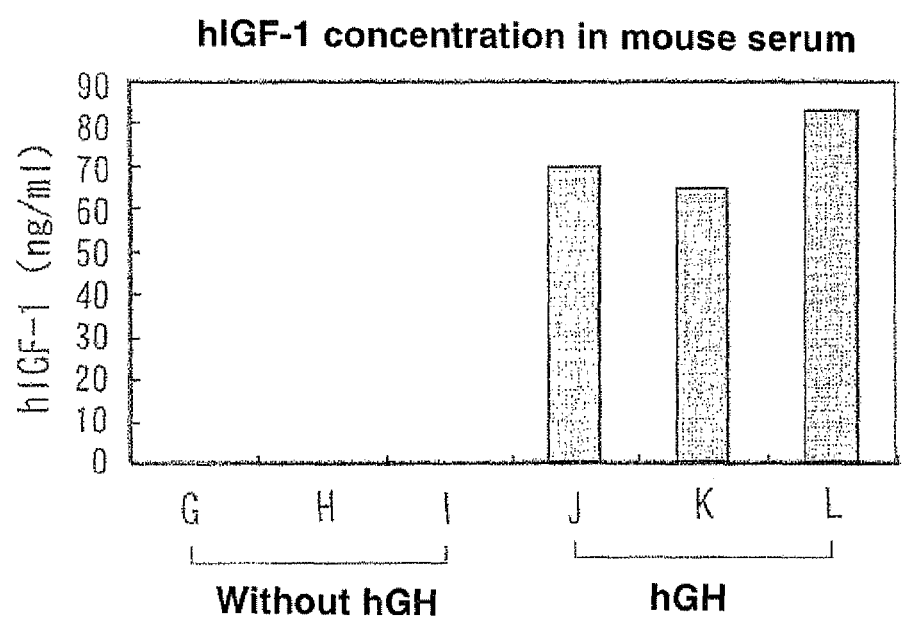
FIG. 5 shows the results showing the hIGF-1 concentration in serum of chimeric mice transplanted with hepatocytes of a female child with and without administration of human growth hormone.

IGF-1 in human blood is detected in an amount of 100 to 350 ng/mL, however, it decreases with aging. It is known that IGF-1 is produced in hepatocytes by the stimulation of growth hormone. It is considered that because there is no stimulation of human growth hormone in chimeric mouse hepatocytes, IGF-1 is not produced. When IGF-1 in the serum of 3 mice without administration of human growth hormone was determined, it was found to be the detection limit or less (<9.4 ng/mL) in all mice. In mice with administration of human growth hormone, IGF-1 was detected in the serum in an amount of 65 to 83 ng/mL (FIG. 5).

Figure 6:
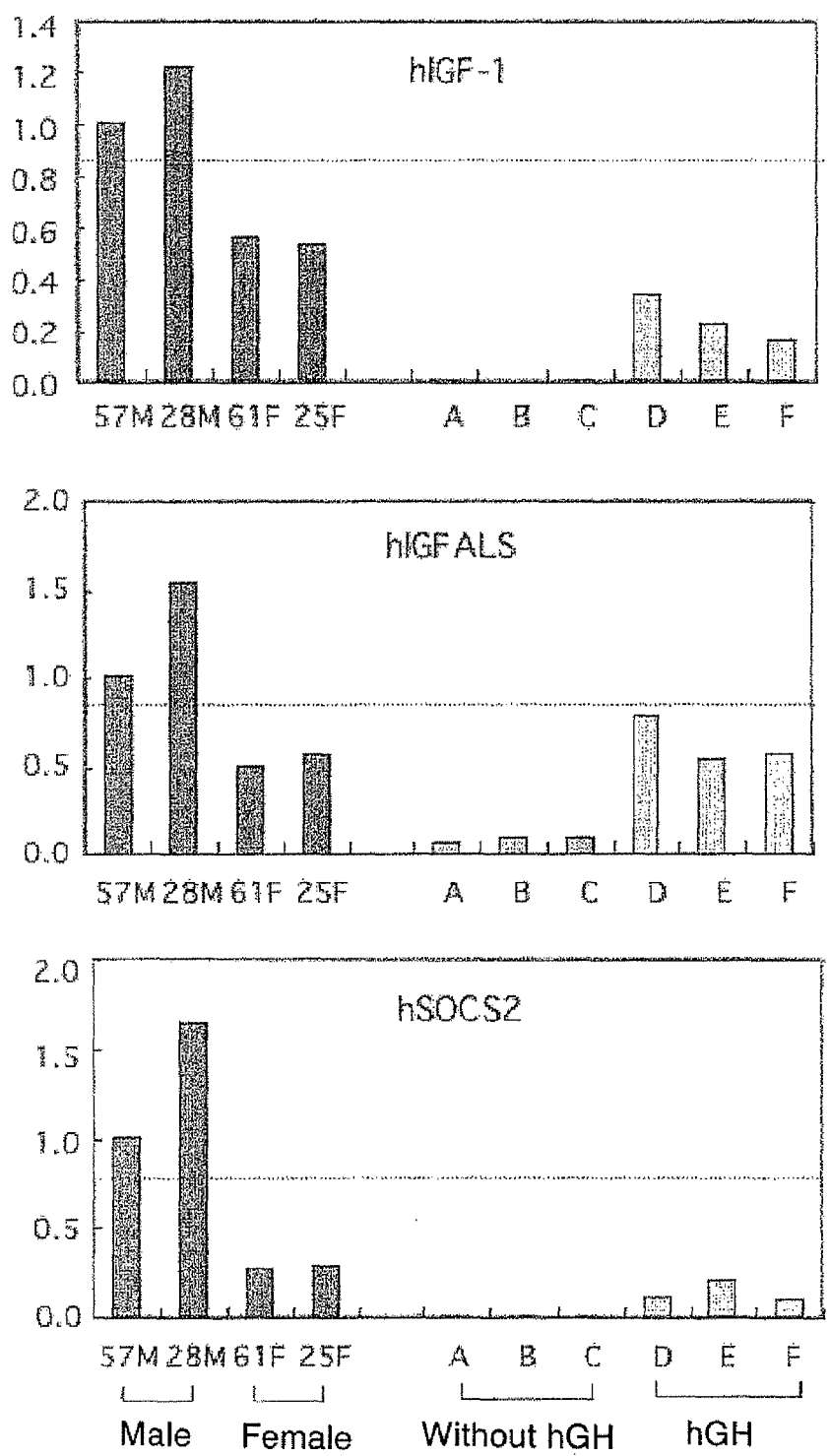
FIG. 6 shows the results showing the expression level of genes whose mRNA expression level increased in chimeric mouse hepatocytes by administering human growth hormone to chimeric mice transplanted with hepatocytes of a male child in human hepatocytes derived from excised liver, and hepatocytes derived from chimeric mice with and without administration of human growth hormone.
Figure 7:
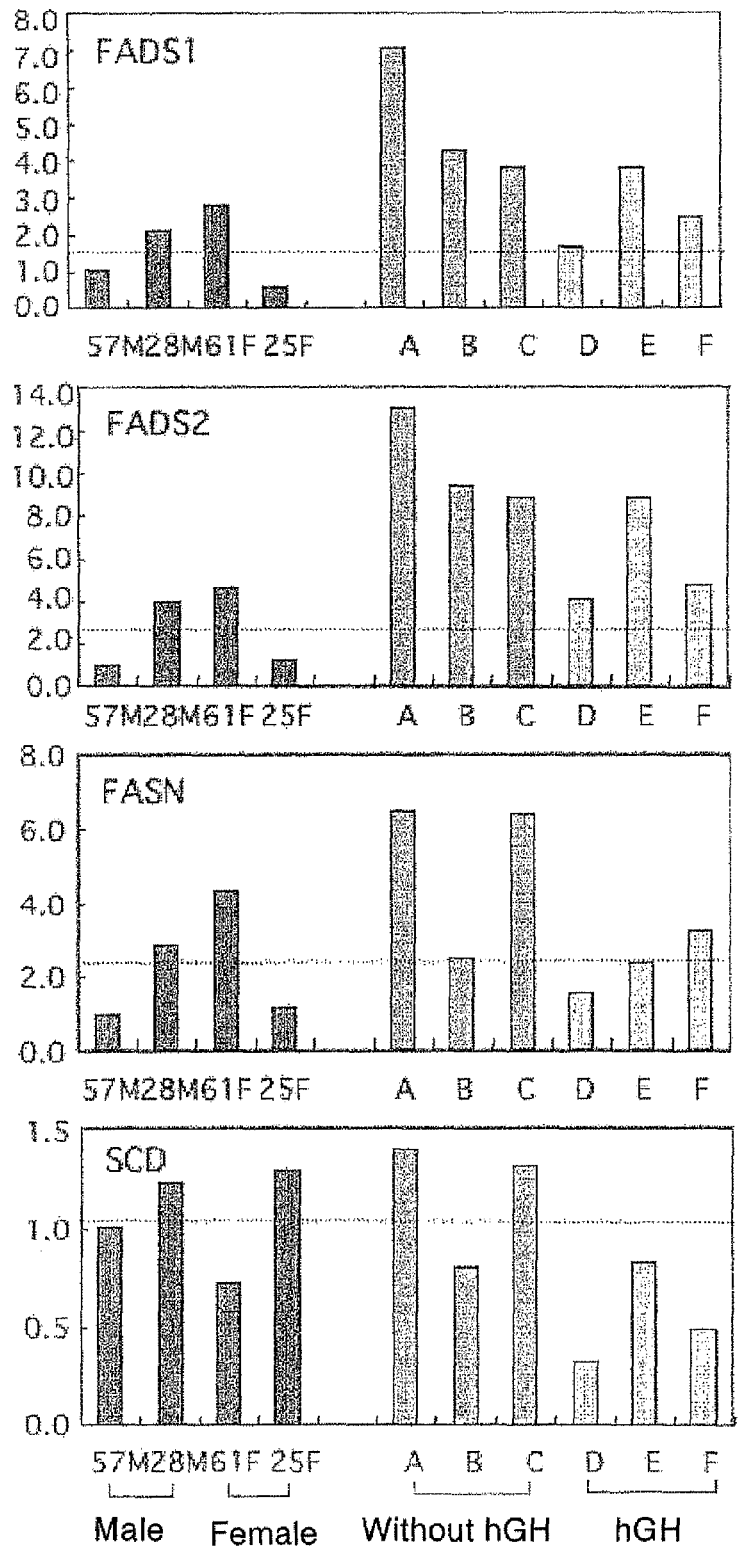
FIG. 7 shows the results showing the expression level of genes involved in lipid synthesis and metabolism of chimeric mice transplanted with hepatocytes of a male child in human hepatocytes derived from excised liver, and hepatocytes derived from chimeric mice with and without administration of human growth hormone.

Hepatocytes were isolated by a collagenase perfusion method from excised liver (4 cases), chimeric mice with administration of growth hormone (3 cases) and chimeric mice without administration (3 cases). When the purity of the isolated hepatocytes was examined by FACS using antibody K8216 specific to human hepatocytes, human hepatocytes were found to be contained at 90% or more. Comparison was performed in terms of the expression level of mRNA of genes IGF-1, IGFALS and SOCS2 whose gene expression is known to be induced by growth hormone. As a result, in the chimeric mice without administration, the expression of any of the genes was significantly lower than in human hepatocytes derived from the excised liver. However, in the chimeric mice with administration of human growth hormone, an expression level of one-third to the same level of the human hepatocytes derived from the excised liver was observed (FIG. 6). Further, the expression of FASN, FADS1, FADS2 and SCD, which are genes involved in lipid synthesis or regulation of unsaturation of fatty acid was also examined. As a result, the expression of FASN, FADS1 and FADS2 was higher in the chimeric mice without administration compared with the human hepatocytes derived from the excised liver. However, in the chimeric mice with administration of human growth hormone, the expression level thereof decreased in a similar manner to that in human hepatocytes derived from the excised liver (FIG. 7). Further, a difference in the expression of SCD between the chimeric mice without administration and the human hepatocytes derived from the excised liver was not observed, however, the expression of SCD decreased in the chimeric mice with administration of human growth hormone.

From the above results, it was presumed that human hepatocytes in the chimeric mice were deficient in growth hormone, therefore a gene involved in lipid synthesis or the like was induced thereby to cause fatty change. By administering human growth hormone to chimeric mice, humanized mouse models showing more normal expression of genes or proteins of human hepatocytes can be produced.

INDUSTRIAL APPLICABILITY

The replacement ratio with adult human hepatocytes in chimeric mice can be increased by about twice or more. This allows the expansion of the applicability of human hepatocyte chimeric mice as a screening system for drug metabolism or toxicity in adult humans, or a screening system for the most suitable therapeutic method for personalized medicine.

Further, fatty liver in human hepatocyte chimeric mice in which about 70% or more of mouse hepatocytes have been substituted with human hepatocytes is ameliorated. This allows a more accurate drug efficacy test or toxicity test in mice with high replacement.

The invention claimed is:

1. A method of increasing the ratio of adult human hepatocytes to mouse hepatocytes in an immunodeficient hepatopathy mouse, comprising the steps of:
    (1) transplanting adult human hepatocytes into the immunodeficient hepatopathy mouse; and
    (2) administering human growth hormone to the mouse transplanted with adult human hepatocytes, wherein the human growth hormone specifically proliferates the transplanted hepatocytes and said ratio is increased by twice or more when compared to the case where human growth hormone is not administered.

2. A method of reducing or removing the accumulation of lipid droplets in the hepatocytes of an immunodeficient hepatopathy mouse transplanted with young human hepatocytes, comprising the step of administering an effective amount of human growth hormone to the mouse transplanted with young human hepatocytes following transplantation.

* * * * *